United States Patent
Marsden

[11] Patent Number: 6,149,666
[45] Date of Patent: Nov. 21, 2000

[54] TOURNIQUET

[75] Inventor: Stewart E. Marsden, Montville, N.J.

[73] Assignee: Becton Dickinson and Company, Franklin Lakes, N.J.

[21] Appl. No.: 09/362,325

[22] Filed: Jul. 27, 1999

[51] Int. Cl.[7] .................................................. A61B 17/00
[52] U.S. Cl. ............................................................ 606/203
[58] Field of Search .................................... 606/203, 202, 606/201, 204; 600/586, 499; 280/801.1; 180/273; 340/573.7; 24/170

[56] References Cited

U.S. PATENT DOCUMENTS

| | | |
|---|---|---|
| 3,628,536 | 12/1971 | Glesne . |
| 3,910,280 | 10/1975 | Talonn . |
| 3,930,506 | 1/1976 | Overend . |
| 4,106,002 | 8/1978 | Hogue, Jr. . |
| 4,273,130 | 6/1981 | Simpson . |
| 4,300,573 | 11/1981 | Rebbe et al. ............................ 600/499 |
| 4,323,232 | 4/1982 | Terpening . |
| 4,384,583 | 5/1983 | Speelman et al. . |
| 4,566,436 | 1/1986 | Loefquist . |
| 4,661,099 | 4/1987 | von Bittera et al. . |
| 4,727,885 | 3/1988 | Ruff . |
| 4,737,885 | 4/1988 | Akutsu . |
| 4,807,753 | 2/1989 | Goldstein . |
| 4,870,978 | 10/1989 | Atwell . |
| 4,911,162 | 3/1990 | Wolff . |
| 4,972,177 | 11/1990 | Nolan ..................................... 340/573.7 |
| 5,015,251 | 5/1991 | Cherubini . |
| 5,074,873 | 12/1991 | Dioguardi . |
| 5,219,356 | 6/1993 | Harreld et al. . |
| 5,272,236 | 12/1993 | Lai et al. . |
| 5,278,272 | 1/1994 | Lai et al. . |
| 5,394,955 | 3/1995 | Howard .................................... 180/237 |
| 5,413,582 | 5/1995 | Eaton . |
| 5,653,728 | 8/1997 | Ahern et al. . |
| 5,692,513 | 12/1997 | Davis et al. ............................. 600/499 |
| 5,807,266 | 9/1998 | Itonaga et al. ........................... 600/499 |

FOREIGN PATENT DOCUMENTS

WO 94/13213 6/1994 WIPO .

*Primary Examiner*—Michael Buiz
*Assistant Examiner*—Jackie Tan-Uyen T. Ho
*Attorney, Agent, or Firm*—Nanette S. Thomas, Esq.; Hoffman & Baron, LLP

[57] ABSTRACT

A tourniquet providing for generation of an alarm signal upon passage of a predetermined time after the tourniquet is placed on the patient's limb. The tourniquet includes an elongate flexible body having a pair of spaced-apart connection locations for attachment to secure the body in circumscribing relationship about the limb. A signal alarm is placed in transmission continuity with the connection locations for establishing a complete transmission circuit upon attachment of the connection locations. The signal alarm is placed in a signal generating condition upon completion of the transmission circuit.

2 Claims, 2 Drawing Sheets

TOURNIQUET

BACKGROUND OF THE INVENTION

1. Field of the Invention

The present invention relates to a tourniquet for temporarily occluding a patient's vein. More particularly, the present invention relates to a tourniquet which may be placed in circumscribing relationship about a patient's limb and which generates a signal after a predetermined period of time indicating that the tourniquet is still in place about the patient's limb.

2. Description of Related Art

A tourniquet is typically used to occlude a patient's vein and enable medical personnel to successfully perform a variety of intravenous procedures. Such procedures include routine medical procedures as a phlebotomy, intravenous catheter insertion, dialysis, blood transfusion, donation, intravenous therapy and infusion set insertion.

Common tourniquets which have been long used for this purpose include a length of elastic material which is circumferentialy placed about the patient's limb and secured and tightened in circumscribing a relationship therearound. Preferably, the tourniquet is secured about the patient's arm by slip knotting the tourniquet or by employing fastening members which may be attached to the tourniquet.

In typical use, a medical technician or phlebotomist will normally place the tourniquet about the upper arm of a patient and apply pressure by tightening. The tourniquet is then fastened in its tightened position to induce swelling in the veins of the lower arm. This causes a vein to stand out providing a convenient site for venepuncture. Once the site is identified, a needle is inserted, the blood sample is removed and the needle is withdrawn. After inserting the needle into the vein, or immediately after withdrawing of the blood, the tourniquet is promptly removed from the patient's arm. Removal of the tourniquet reestablishes proper blood flow through the patient's limb.

Leaving the tourniquet in place over an extended period of time, results in prolonged venostasis which may lead to an increased incidence of pre-analytical errors, unexplained analytical results, as well as discomfort and potential long term injurious results to the patient. The prompt removal of the tourniquet from the patient's limb is typically left to the memory of the medical technician conducting the procedure or to the patient from whom the blood is drawn. In certain situations due to distractions which may commonly occur in hospital and laboratory settings, it may be possible for the tourniquet to remain on the patient longer than is desirable.

Certain tourniquets have been developed which allow selective pressure levels to be applied to the patient's limbs. Many of these tourniquets provide pressure monitors to monitor the pressure applied to assure that it falls within a predetermined minimum and maximum pressure level. If the pressure falls outside the predetermined range, the sensor may emit an alarm alerting the technician. However, these pressure monitoring devices require complex mechanical and electrical equipment such as electrical wires, gauges, pressure supply lines and the like. None of these devices may be employed in a disposable tourniquet situation.

Therefore, it is desirable to provide an inexpensive throwaway or disposable tourniquet which can be easily used and which would avoid problems experienced with leaving the tourniquet in place over an extended period of time.

SUMMARY OF THE INVENTION

The present invention provides a tourniquet for positioning in circumscribing relationship about a patient's limb which emits a signal after the tourniquet has been left on the limb for a predetermined period time.

The tourniquet of the present invention includes an elongate flexible body have a pair of spaced apart connection locations for mutual attachment to secure the body in wrapping conformity about the limb. A signal alarm assembly is placed in transmission continuity with the connection locations for establishing a complete transmission circuit upon attachment of the connection locations. The signal alarm assembly is placed in a signal generating condition upon completion of the transmission circuit.

Preferably, an audio alarm is provided which emits a first audio signal upon passage of a first predetermined time after the tourniquet is attached around the patient's limb. Also, additional audio signals may be emitted after the passage of subsequent predetermined periods of time.

Electrical connection of the signal alarm assembly is achieved upon mechanical attachment of the tourniquet about the patient's arm. Such mechanical and electrical connection may be provided by cooperating snap fasteners positioned at spaced apart locations on the tourniquet body.

The present invention provides an alarm which alerts the medical technician, as well as the patient, that the tourniquet is still in place after completion of the medical procedure. Preferably the present invention provides an alarm which emits an audio signal upon passage of a predetermined period of time after the tourniquet is applied.

The attributes of the present invention include that it is an inexpensive, reusable, throw-away or disposable tourniquet and alerts the patient and user to the amount of time that the tourniquet is in use with a patient.

DETAILED DESCRIPTION

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

Figure 1:
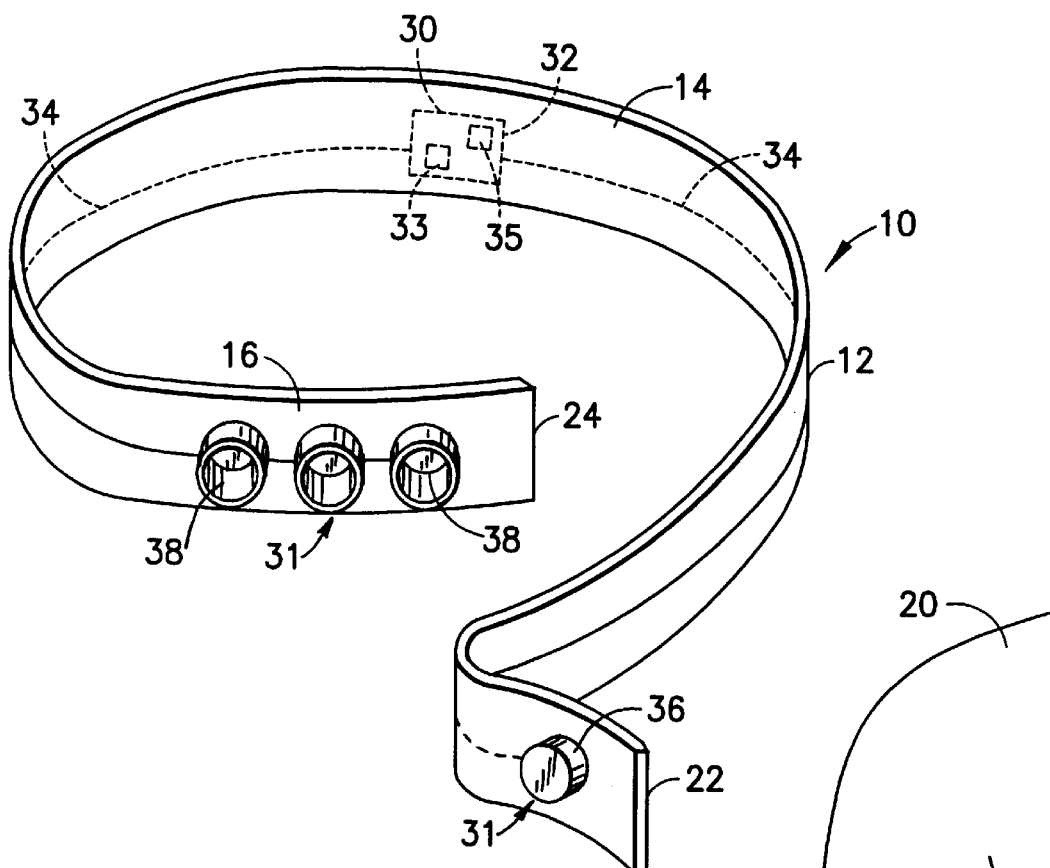
FIG. 1 is a perspective view of the tourniquet of the present invention.
Figure 2:
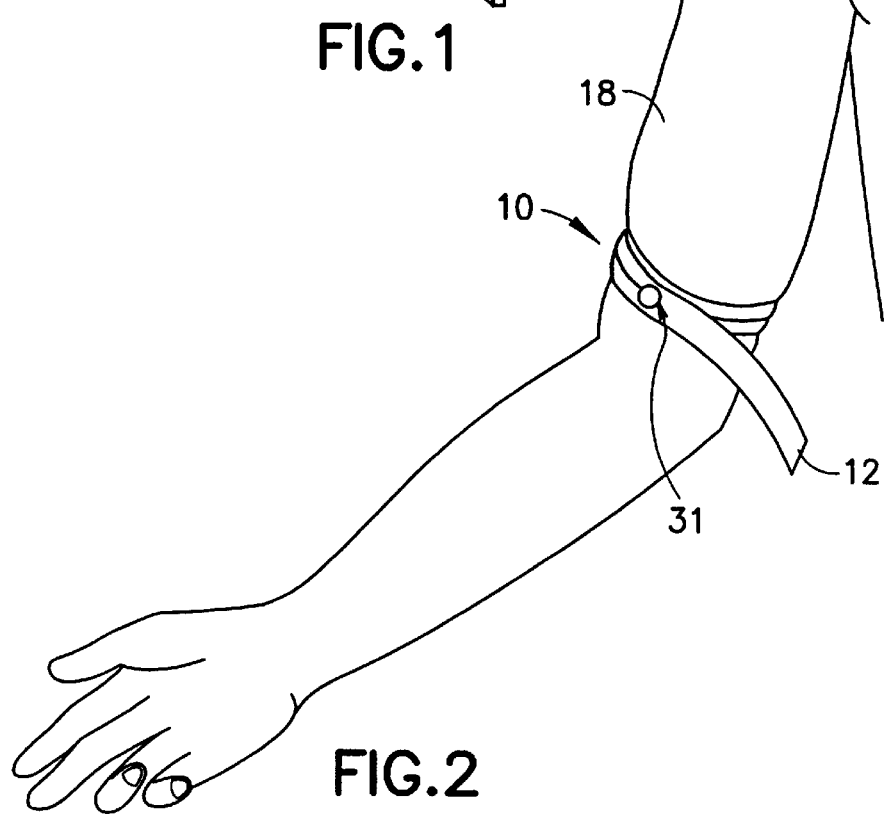
FIG. 2 is a perspective view of the tourniquet of FIG. 1 applied to a patient's arm.
Figure 3:
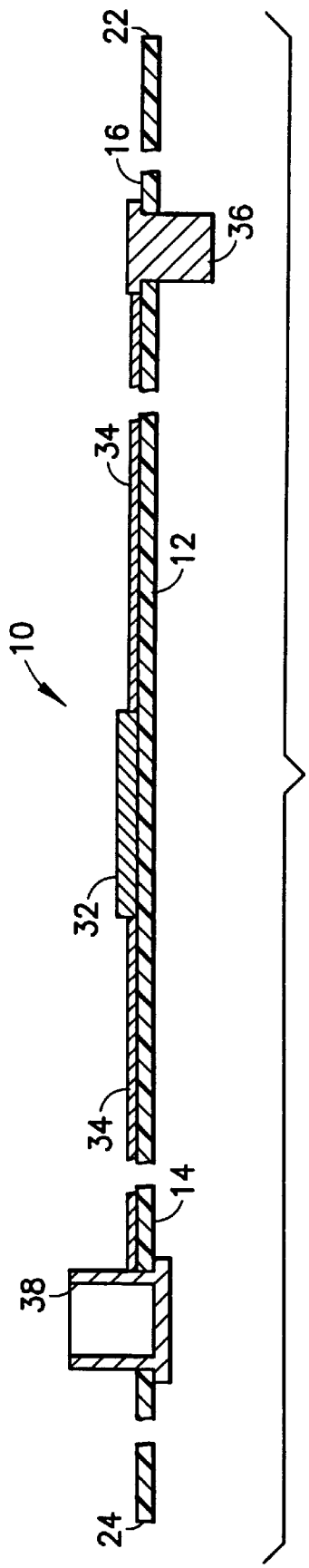
FIG. 3 is a side elevational view of the tourniquet of FIG. 1, taken along line 3—3 thereof.

Referring to FIGS. 1—3, a tourniquet 10 of the present invention is shown. Tourniquet 10 includes a tourniquet body 12 formed of an elongated strip of a relatively elastic material. Tourniquet 10 includes opposed surfaces defined as inner surface 14 and outer surface 16 when viewed as applied to the upper arm 18 of a patient 20. The body 12 further defines opposed ends 22 and 24. The strip of material forming body 12 may be of various sizes, preferably about ¾ of an inch to an inch ½ wide and about 12 inches to about 30 inches in length after cutting and finishing. The thickness of material may be between 0.006 inches and 0.024 inches. The tourniquet further includes an alarm assembly 30.

The tourniquet art, the tourniquet body 12 may be formed of various elastomeric materials including both latex and non-latex materials. Common non-latex materials include mono elastomers, polyurethane elastomers, polypropylene elastomers, styrenic elastomers, metallocene elastomers, and polyolefin elastomers.

Thermoplastic elastomers forming tourniquet 10 may be treated with an additive comprising slip and antiblock components. The slip components may include oils, waxes, stearic acid while the antiblock components may include silica or carbon. The slip component provides frictional characteristics to the disposable tourniquet while the antiblock component allows the tourniquet body to be formed on a roll without adhering to itself.

As shown in FIGS. 1—3, alarm assembly 30 may preferably include a microchip 32 which may be embedded into or attached to outer surface 16 of tourniquet body 12. Microchip 32 may include microelectronics and an audio signal generator 33 which emits an audio alarm. Microchip 32 may be connected via an electronic lead 34, also in embedded or attached to outer surface 16 of tourniquet body 12, to cooperating fasteners 31 adjacent the ends 22 and 24 of tourniquet body 12. Fasteners 31 provide for attachment of the tourniquet about the patient's arm in a tightened condition to effect occlusion of the vein. Fasteners 31 further establish electrical continuity via lead 34 to microchip 32.

As also shown in FIGS. 1 and 3, alarm assembly 30 includes microchip 32 and lead 34 as attached to outer surface 16 of tourniquet body 12. Microchip 32 is positioned at a central location along the length of body 12 with lead 34 extending in opposite directions therefrom towards both ends 22 and 24. Alarm assembly 30 further includes an attachment mechanism in the form of cooperating male and female snap fasteners 36 and 38 respectively. Snap fasteners 36 and 38 are preferably formed of a metallic material which has a high electrical conductivity so that when the male snap fastener 36 is connected to the female snap fastener 38, a complete electrical circuit is established between the fasteners and the microchip. In a preferred embodiment shown in FIG. 1, a plurality of spaced-apart female snap fasteners 38 are shown. Spaced-apart female snap fasteners 38 permit the tourniquet to be adjustably positioned in circumscribing relationship about the patient's arm to provide the requisite degree of tightness therearound. Other techniques for providing adjustable tightening of the tourniquet may also be employed. Male and female snap fasteners 36 and 38 establish an electrical connection therebetween in order complete the electrical circuit and secure the tourniquet about the patient's arm. Once the electrical circuit is completed, alarm assembly 30 is placed in a signal generating condition.

The tourniquet may provide plural distinct alarm signals at different predetermined times once in the signal generating condition. For example, the tourniquet may be secured about the patient's arm as shown in FIG. 2 with male snap fastener 36 being secured to female snap fastener 38. This completes the electrical circuit. Microchip 32 further includes a timer 35 which upon completion of the circuit is activated. Timer 35 provides a delay such that after a predetermined period of time, for example one minute, an audio signal such as a single "beep" is generated. Timer 35 may also provide a second delay so that after passage of a second period of time, for example two minutes from timer activation, a second audio signal such as a repetitive "beep" is generated. It is still further contemplated that timer 35 may also provide a further delay such that after a passage of a third period of time, for example three minutes, a continuous audio signal is generated. These various signals alert both the medical technician as well as the patient that the tourniquet is still in place about the patient's arm so that the tourniquet may be promptly removed.

The type of audio signals as well as the time delay at which the signal is generated is described here by way of examples. Microchip 32 and timer 35 may be modified to include a wide variety of audio signals at various desirable periods of time.

While the present invention describes, an electronic microchip attached via an electrical lead to a mechanical and electrical snap connection, other circuit arrangements are also within the contemplation of the present invention. For example, an LED may be employed alone or in combination with the audio alarm provide a visual indication that the tourniquet has remained in place for a certain period of time. Further, while electrical components are used to create an electrical circuit, other signal generating circuits are also within the contemplation of the present invention.

What is claimed is:

1. A tourniquet comprising:
    an elongate flexible body having a pair of spaced-apart connection locations for mutual attachment to secure said body in wrapping conformity about a limb; and a signal alarm assembly in transmission continuity with said connection locations for establishing a complete transmission circuit upon said attachment of said connection locations;
    said signal alarm assembly being placed in a signal generating condition upon said completion of said transmission circuit and comprising a signal generator for emitting an audio signal and a timer for causing said signal generator to emit plural audio signals upon passage of a plural predetermined time periods after completion of said transmission circuit.

2. The tourniquet of claim 1, wherein said connection locations include cooperating snap fasteners for establishing releasable mechanical and electrical connection between said spaced apart locations of said body.

* * * * *